(12) United States Patent
Hefti et al.

(10) Patent No.: US 6,586,946 B2
(45) Date of Patent: Jul. 1, 2003

(54) SYSTEM AND METHOD FOR DETECTING AND IDENTIFYING MOLECULAR EVENTS IN A TEST SAMPLE USING A RESONANT TEST STRUCTURE

(75) Inventors: John Hefti, San Francisco, CA (US); Hong Peng, Fremont, CA (US)

(73) Assignee: Signature BioScience, Inc., San Francisco, CA (US)

( * ) Notice: Subject to any disclaimer, the term of this patent is extended or adjusted under 35 U.S.C. 154(b) by 0 days.

(21) Appl. No.: 09/775,710

(22) Filed: Feb. 1, 2001

(65) Prior Publication Data

US 2002/0149377 A1 Oct. 17, 2002

Related U.S. Application Data

(60) Provisional application No. 60/248,298, filed on Nov. 13, 2000.

(51) Int. Cl.[7] .......................... G01R 27/04; G01R 27/32
(52) U.S. Cl. ...................................................... 324/636
(58) Field of Search ................................ 324/667, 668, 324/675, 674, 676, 682, 708, 707, 710, 425, 436, 442, 315, 633, 653, 652, 636

(56) References Cited

U.S. PATENT DOCUMENTS

| | | | | |
|---|---|---|---|---|
| 4,593,248 A | * | 6/1986 | Hyde et al. .................. | 324/300 |
| 4,829,233 A | * | 5/1989 | Flemming et al. ........... | 324/632 |
| 5,025,222 A | * | 6/1991 | Scott et al .................... | 324/633 |
| 5,187,096 A | | 2/1993 | Giaever et al. .............. | 435/291 |
| 5,233,306 A | | 8/1993 | Misra .......................... | 324/601 |
| 5,786,893 A | * | 7/1998 | Fink et al. ................... | 356/301 |
| 5,846,708 A | | 12/1998 | Hollis et al. .................... | 435/6 |
| 5,852,229 A | * | 12/1998 | Josse et al. .................. | 310/365 |
| 5,989,402 A | | 11/1999 | Chow et al. ................. | 204/601 |
| 6,023,170 A | | 2/2000 | Hilhorst et al. .............. | 324/689 |
| 6,111,414 A | * | 8/2000 | Chatterjee et al. ........... | 324/633 |
| 6,166,551 A | * | 12/2000 | Scott et al. .................. | 324/602 |
| 6,359,444 B1 | * | 3/2002 | Grimes ........................ | 324/633 |

FOREIGN PATENT DOCUMENTS

| | | |
|---|---|---|
| DE | 199 16 867 A | 10/2000 |
| EP | 0 519 250 A | 12/1992 |
| WO | WO 99 39190 | 8/1999 |
| WO | WO 00/45170 | 8/2000 |
| WO | WO 00/77501 | 12/2000 |
| WO | WO 01/27610 | 4/2001 |

OTHER PUBLICATIONS

Hefti et al., "Sensitive Detection Method of Dielectric Dispersions in Aqueous–Based, Surface–Bound Macromolecular Structures Using Microwave Spectroscopy" Applied Physics Letters, American Institute of Physics, New York, US, vol. 75, No. 12, pp. 1802–1804 (1999).

Altschuler, H.M. 1963. Dielectric Constant. Handbook of Microwave Measurements (M. Sucher & J. Fox, eds.). Brooklyn Polytechnic Press, New York, NY. Vo. 2:530–536.

Gallone, "A Fast and Precise Method for the Measurement of Dielectric Permittivity at Microwave Frequencies", Journal of Microwave Power and Electromagnetic Energy, 3(3):158–164 (1996).

* cited by examiner

*Primary Examiner*—N. Le
*Assistant Examiner*—John Teresinski
(74) *Attorney, Agent, or Firm*—Clifford B. Perry; Kelvan Patrick Howard

(57) ABSTRACT

A system and method for detecting a molecular event in a test sample using a resonant test structure is presented. The method includes providing a resonant test structure having a resonant response associated therewith. Next, a first resonant response of the resonant test structure is obtained when the resonant test structure is electromagnetically coupled to a reference sample, the reference sample having a known composition. A second resonant response is also obtained when the resonant test structure is electromagnetically coupled to the test sample, the test sample having an unknown composition. Subsequently, one or more first electrical parameters, such as the q-factor of the resonator, are derived from the first resonant response. One or more second electrical parameters are similarly derived from the second resonant response. The similarity or difference between the first and second electrical parameters are analyzed to determine the presence or absence of the molecular event in the test sample.

31 Claims, 11 Drawing Sheets

| Record ID | Molecular Event ID | Test Structure ID | $Q_{ref}$ | $f_{ref}$ (GHz) | Signal Input Pwr (dBm) | Sample Temp (deg. F) |
|---|---|---|---|---|---|---|
| 0010 | BSA(PBS) | Coax 003 | 1070 | 1.209 | -15 | 27.63 |
| 0408 | RNASE(DI) | Cav 002 | 1502 | 12.81 | -13 | 28.17 |
| 0633 | HSA+SAL(DI) | Coax 003 | 1025 | 1.391 | -14 | 26.79 |
| 0833 | HSA(PBS) | Ring 010 | 803 | .691 | -13 | 27.22 |
| 1029 | PBS | Stub 022 | 573 | .812 | -15 | 27.84 |

*FIG. 6*

SYSTEM AND METHOD FOR DETECTING AND IDENTIFYING MOLECULAR EVENTS IN A TEST SAMPLE USING A RESONANT TEST STRUCTURE

CROSS REFERENCE TO RELATED APPLICATIONS

This application claims the benefit of U.S. Provisional Application No. 60/248,298, entitled "System and Method for Real-Time Detection of Molecular Interactions," filed Nov. 13, 2000.

BACKGROUND OF THE INVENTION

The present invention is related to the systems and methods for characterizing the molecular make-up an unknown sample, and more particularly to systems and methods for detecting and identifying molecular events in a sample using a resonant test structure.

Virtually every area of biological science is in need of a system to determine the ability of molecules of interest to interact with other molecules. Likewise, the ability to detect the presence and/or physical and functional properties of biological molecules on a small scale is highly desirable. Such molecular interactions, as well as the detection of functional and physical properties of molecules, are referred to here as molecular events. The need to detect molecular events ranges from the basic science research lab, where chemical messenger pathways are being mapped out and their functions correlated to disease processes, to pre-clinical investigations, where candidate drugs are being evaluated for potential in vivo effectiveness. The need to detect physical and functional properties is also present in these research areas, such as for functional analysis of a newly discovered protein or of a genetic (or synthetic) variant of a molecule of know biological importance. Other areas that benefit from a better understanding of molecular events include pharmaceutical research, military applications, veterinary, food, and environmental applications. In all of these cases, knowledge of the ability of a particular analyte to bind a target molecule is highly useful, as is information relating to the quality of that binding (e.g., affinity and on-off rate), and other functional information about new molecules, particularly when information can be obtained from a small amount of sample.

Numerous methodologies have been developed over the years in attempts to meet the demands of these fields, such as Enzyme-Linked Immunosorbent Assays (ELISA), Radio-Immunoassays (RIA), numerous fluorescence assays, nuclear magnetic resonance (NMR) spectroscopy, and calorimetric assays, as well as a host of more specialized assays. Most of these assay techniques require specialized preparation, purification, or amplification of the sample to be tested. To detect a binding event between a ligand and an antiligand, for example, a detectable signal is required that signals the existence or extension of binding. Usually the signal has been provided by a label that is attached to either the ligand or antiligand of interest. Physical or chemical effects which produce detectable signals, and for which suitable labels exist, include radioactivity, fluorescence, chemiluminescence, phosphorescence and enzymatic activity, to name a few. The label can then be detected by spectrophotometric, radiometric, or optical tracking methods.

Unfortunately, in many cases it is difficult or even impossible to label one or all of the molecules needed for a particular assay. The presence of a label also can make the molecular recognition between two molecules not function in its normal manner for many reasons, including steric effects. In addition, none of these labeling approaches determines the exact nature of the binding event, so that, for example, active-site binding to a receptor is indistinguishable from non-active-site binding, such as allosteric binding, and thus no functional information is obtained via the present detection methodologies. In general, limitations also exist in the areas of specificity and sensitivity of most assay systems. Cellular debris and non-specific binding often cause an assay to be noisy and make it difficult or impossible to extract useful information. As mentioned above, some systems are too complicated to allow the attachment of labels to all analytes of interest or to allow an accurate optical measurement to be performed. Therefore, a practical, economic, and universal detection technique that can directly monitor without a label, in real time, the presence of analytes, for instance, the extent, function and type of binding events that are actually taking place in a given system would represent a significant breakthrough.

In particular, the biomedical industry needs an improved general platform technology that has very broad applicability to a variety of water-based or other fluid-based physiological systems, such as nucleic acid binding, protein-protein interactions, and small molecule binding, as well as other compounds of interest. Ideally, the assay should not require highly specific probes, such as specific antibodies or exactly complementary nucleic acid probes. It should be able to work in native environments, such as whole blood or cytosolic mixtures, as well as other naturally occurring systems. It should operate by measuring the native properties of the molecules and not require additional labels or tracers to actually monitor the binding event. For some uses it should be able to provide information on the nature of the binding event, such as whether or not a given compound binds to the active site as an agonist or an antagonist on a particular drug receptor or if the given compound binds to an allosteric site, and not function simply as a marker to indicate whether or not the binding event has taken place. For many applications, it should be highly miniaturizable and highly parallel, so that complex biochemical pathways can be mapped out, or so that extremely small and numerous quantities of combinatorial compounds can be used in drug screening protocols. In many applications, it should further be able to monitor in real time a complex series of reactions, so that accurate kinetics and affinity information can be obtained almost immediately. Perhaps most importantly, for most commercial applications it should be inexpensive and easy to use, with few sample preparation steps, affordable electronics and disposable components, such as surface chips for bioassays that can be used for an assay and then thrown away, and it should be highly adaptable to a wide range of assay applications.

Accordingly, there exists a need for development of methods of detecting molecular events that do not require labels such as fluorophores or radioisotopes, that are quantitative and qualitative, that are specific to the molecule of interest, that are highly sensitive, and that are relatively simple to implement. The present invention fulfills many of the needs discussed above and others as well, as described herein.

SUMMARY OF THE INVENTION

The present invention provides methods and systems for detecting and identifying molecular events in a test sample without the use of labels. The method includes providing a resonant test structure having a resonant response associated therewith. A first resonant response of the resonant test structure is obtained when the resonant test structure is electromagnetically coupled to a reference sample, the reference sample having a known composition. A second resonant response is also obtained when the resonant test structure is electromagnetically coupled to the test sample having unknown composition. Subsequently, one or more first electrical parameters (the q-factor of the resonant test structure in one embodiment) are derived from the first resonant response. One or more second electrical parameters are similarly derived from the second resonant response. The similarity or difference between the first and second electrical parameters are analyzed to determine the presence or absence of the molecular event in the test sample.

The nature and advantages of the present invention will be better understood with reference to the following drawings and detailed description.

BRIEF DESCRIPTION OF THE DRAWINGS

FIG. 6 illustrates one embodiment of a reference sample database in accordance with the present invention.

DESCRIPTION OF THE SPECIFIC EMBODIMENTS

Definition of Terms

Figure 1:
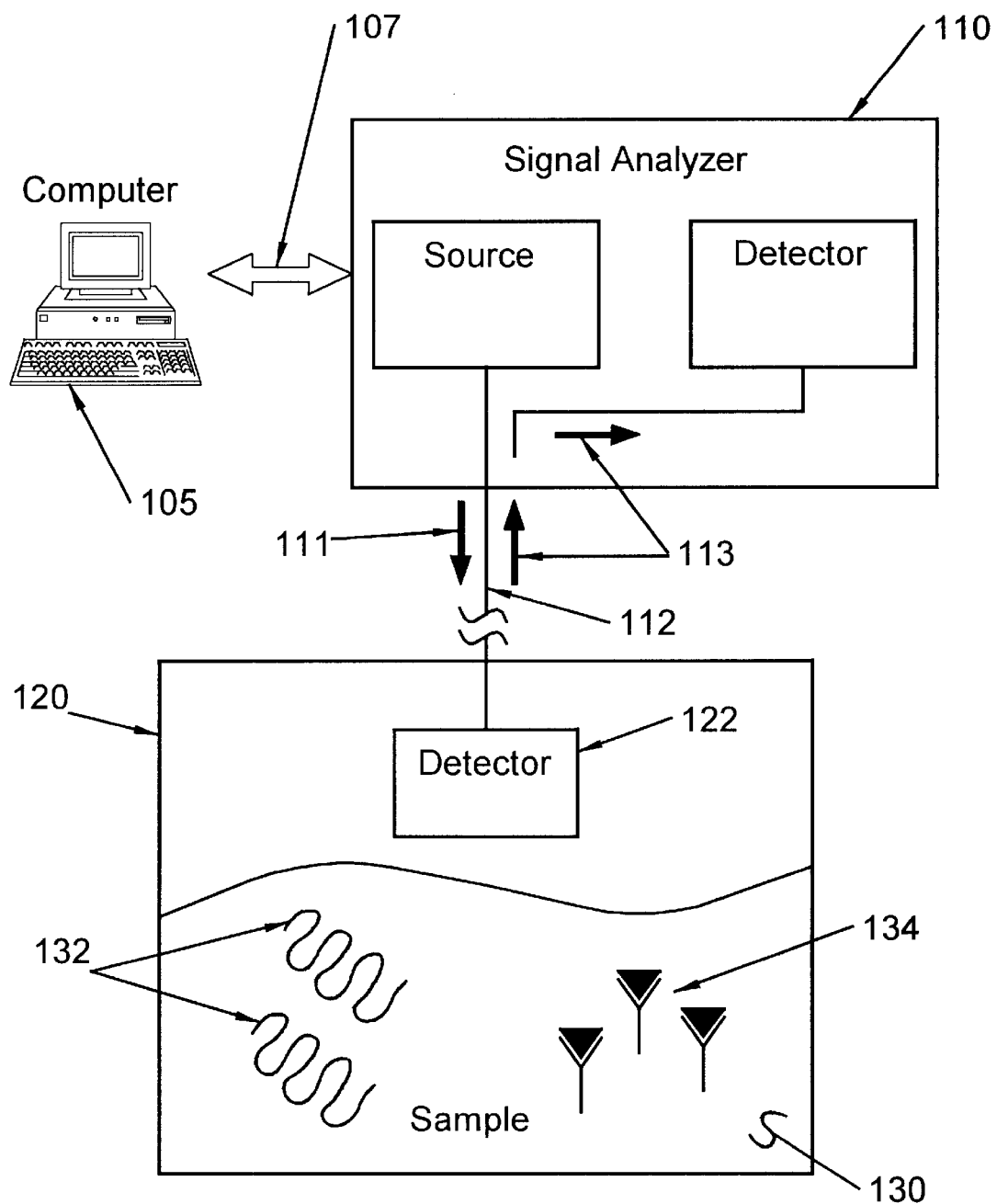
FIG. 1 illustrates a test system configured to measure the permittivity of the test sample in accordance with one embodiment of the present invention.

As used herein, the term "molecular binding event" (sometimes shortened to "binding event" or "binding") refers to the interaction of a molecule of interest with another molecule. The term "molecular structure" refers to all structural properties of molecules of interest, including the presence of specific molecular substructures (such as alpha helix regions, beta sheets, immunoglobulin domains, and other types of molecular substructures), as well as how the molecule changes its overall physical structure via interaction with other molecules (such as by bending or folding motions), including the molecule's interaction with its own solvation shell while in solution. Together, "molecular structures" and "molecular binding events" are referred to as "molecular events." The simple presence of a molecule of interest in the region where detection/analysis is taking place is not considered to be a "molecular event," but is referred to as a "presence."

Examples of molecular binding events are (1) simple, non-covalent binding, such as occurs between a ligand and its antiligand, and (2) temporary covalent bond formation, such as often occurs when an enzyme is reacting with its substrate. More specific examples of binding events of interest include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Binding events can occur as primary, secondary, or higher order binding events. A primary binding event is defined as a first molecule binding (specifically or non-specifically) to an entity of any type, whether an independent molecule or a material that is part of a first surface, typically a surface within the detection region, to form a first molecular interaction complex. A secondary binding event is defined as a second molecule binding (specifically or non-specifically) to the first molecular interaction complex. A tertiary binding event is defined as a third molecule binding (specifically or non-specifically) to the second molecular interaction complex, and so on for higher order binding events.

Examples of relevant molecular structures are the presence of a physical substructure (e.g., presence of an alpha helix, a beta sheet, a catalytic active site, a binding region, or a seven-trans-membrane protein structure in a molecule) or a structure relating to some functional capability (e.g., ability to function as an antibody, to transport a particular ligand, to function as an ion channel (or component thereof), or to function as a signal transducer).

Structural properties are typically detected by comparing the signal obtained from a molecule of unknown structure and/or function to the signal obtained from a molecule of known structure and/or function. Molecular binding events are typically detected by comparing the signal obtained from a sample containing one of the potential binding partners (or the signals from two individual samples, each containing one of the potential binding partners) to the signal obtained from a sample containing both potential binding partners. Together, the detection of a "molecular binding event" or "molecular structure" is often referred to as "molecular detection."

The methodology and apparatuses described herein are primarily of interest to detect and predict molecular events of biological and pharmaceutical importance that occur in physiological situations (such as in a cellular or subcellular membrane or in the cytosol of a cell). Accordingly, structural properties of molecules or interactions of molecules with each other under conditions that are not identical or similar to physiological conditions are of less interest. For example, formation of a complex of individual molecules under non-physiological conditions, such as would be present in the vacuum field of an electron microscope, would not be considered to be a preferred "molecular binding event," as this term is used herein. Here preferred molecular events and properties are those that exist under "physiological conditions," such as would be present in a natural cellular or intercellular environment, or in an artificial environment, such as in an aqueous buffer, designed to mimic a physiological condition. It will be recognized that local physiological conditions vary from place to place within cells and organisms and that artificial conditions designed to mimic such conditions can also vary considerably. For example, a binding event may occur between a protein and a ligand in a subcellular compartment in the presence of helper proteins and small molecules that affect binding. Such conditions may differ greatly from the physiological conditions in serum, exemplified by the artificial medium referred to as "normal phosphate buffered saline" or PBS. Preferred conditions of the invention will typically be aqueous solutions at a minimum, although some amounts of organic solvents, such as DMSO, may be present to assist solubility of some components being tested. An "aqueous solution" contains at least 50 wt. % water, preferably at least 80 wt. % water, more preferably at least 90 wt. % water, even more preferably at least 95 wt. % water. Other conditions, such as osmolality, pH, temperature, and pressure, can and will vary considerably in order to mimic local conditions of the intracellular environment in which, for example, a binding event is taking place. The natural conditions in, for example, the cytosol of a cell and a lysosome of that cell, are quite different, and different artificial media would be used to mimic those conditions. Examples of artificial conditions designed to mimic natural ones for the study of various biological events and structures are replete in the literature. Many such artificial media are sold commercially, as exemplified by various scientific supply catalogues, such as the 2000/2001 issue of the Calbiochem General Catalogue, pages 81–82, which lists 60 commercially available buffers with pH values ranging from 3.73 to 9.24 typically used in biological investigations. Also see general references on the preparation of typical media, such as chapter 7 ("The Culture Environment") of *Culture of Animal Cells: A Manual of Basic Techniques*, Third Edition, R. Ian Freshney, Wiley-Liss, New York (1994).

Although most measurements described herein occur to individual molecules or pairs in solution, at some times the method of the invention can be applied to situations in which one of the members of a binding pair is immobilized on a surface at the site of the channel receiving electromagnetic radiation while test compounds are allowed to flow past the immobilized molecule. As used herein, when one member of a binding pair is immobilized, the term "antiligand" is usually used to refer to the molecule immobilized on the surface. The antiligand, for example, can be an antibody and the ligand can be a molecule such as an antigen that binds specifically to the antibody. In the event that the antigen is bound to the surface and the antibody is the molecule being detected, for the purposes of this document the antibody becomes the ligand and the antigen is the antiligand. Alternatively, once an antiligand has bound to a ligand, the resulting antiligand/ligand complex can be considered an antiligand for the purposes of subsequent binding.

As used herein, the term "test signal" refers to an ac time varying signal. In specific embodiments, the test signal is preferably at or above 10 MHz ($10 \times 10^6$ Hz), such as 20 MHz, 45 MHz, 100 MHz, 250 MHz, 500 MHz, 750 MHz, 1 GHz ($1 \times 10^9$ Hz), 2 GHz, 5 GHz, 7.5 GHz, 10 GHz, 12 GHz, 15 GHz, 18 GHz, 20 GHz, 22 GHz, 25 GHz, 28 GHz, 30 GHz, 32 GHz, 40 GHz, 44 GHz, 50 GHz, 60 GHz, 110 GHz, 200 GHz, 500 GHz, 1000 GHz and range anywhere therebetween. A preferred region is from 10 MHz to 40 GHz, and more particularly from 45 MHz to 20 GHz.

As used herein, the term "signal path" refers to the transmission media along which the test signal propagates. A non-exhaustive list of "signal paths" include dielectric and conductive waveguides, multiple conductor structures such as those which support transverse-electromagnetic (TEM) signals, transmission lines with three or more conductive elements which support transverse-electric (TE), transverse-magnetic (TM) or TEM signals such as quadrapolar or octupolar lines, coupled waveguides, resonant cavity, other non-modal structures such as wires, conductive traces in printed circuit boards, other distributed or lumped element circuit structures, and the like.

As used herein, the term "electromagnetically coupled" will generally refer to the transfer of electromagnetic energy of between two or more structures. The term "directly coupled" will be used to describe the arrangement in which the components at issue (e.g., the molecular event and the transmission line) come into direct contact and transfer electromagnetic energy between them. The term "indirectly coupled" will be used to describe the arrangement in which the components are physically separated (e.g., through a matrix layer or barrier deposited along the transmission line, through the material which makes up a microfluidic channel or PTFE flow tube, or through the aqueous environment of the sample in which the molecular is located) but remain electromagnetically coupled to each other.

As used herein, the term "test signal" refers to an ac time varying signal. In specific embodiments, the test signal is preferably at or above 10 MHz ($10 \times 10^6$ Hz), such as 20 MHz, 45 MHz, 100 MHz, 250 MHz, 500 MHz, 750 MHz, 1 GHz ($1 \times 10^9$ Hz), 2 GHz, 5 GHz, 7.5 GHz, 10 GHz, 12 GHz, 15 GHz, 18 GHz, 20 GHz, 22 GHz, 25 GHz, 28 GHz, 30 GHz, 32 GHz, 40 GHz, 44 GHz, 50 GHz, 60 GHz, 110 GHz, 200 GHz, 500 GHz, 1000 GHz and range anywhere therebetween. A preferred region is from 10 MHz to 40 GHz, and more particularly from 45 MHz to 20 GHz.

As used herein, the term "test sample" refers to the bulk material in which the molecular event being detected is located (or is suspected of being located). The test sample is interrogated by test signal, and the presence or absence of the molecular event is detected as a result of interaction of the molecular event in the sample with the test signal. The bulk material can comprise a solid, liquid, or gas, with liquids (and specifically water) being preferred, as most molecular events of interest occur naturally in an aqueous environment. In most (but not all) cases, if a gas is present it will be dissolved in a liquid, while if a solid is present, it will be particulate and serves as a surface that transports one or more components of a binding reaction into the detection region after the component or components have become bound or attached to the solid in another location or that remains in the detection region after other components have been removed. Gases can also be used as transport media (e.g., bubbles that separate liquid phases or that move particulate materials) and can be present as the environment that remains after removal of a liquid (e.g., by filtering or otherwise removing a liquid from a solid phase transporting material). Solid phase sample components can comprise naturally occurring materials including carbohydrates, proteins, oligonucleotides, $SiO_2$, GaAs, and Au or, alternatively, synthetic materials including organic polymers such as Nylon®, Rayon®, Dacryon®, polypropylene, polystryrene, Teflon®, Neoprene, and Delrin. Liquid phase sample components can include an aqueous, organic or inorganic primary component and can exist as simple liquids or be a component of a gel or emulsion. Exemplary sample components include celluloses, dextran derivatives, aqueous solution of d-PBS, Tris and other buffer media, deionized water, DMSO, blood, cerebrospinal fluid, urine, saliva, other physiological fluids, other aqueous solutions containing water, and organic solvents such as ethanol. Pretreatment of a more general sample (by dilution, extraction, etc.) once it is obtained from a source material does not prevent the material from being referred to as a sample.

General Overview

The present invention makes use of the observation that a vast number of molecules can be distinguished based upon their unique dielectric properties. These unique dielectric properties can be observed by coupling a test signal to a test sample that includes a molecular structure or binding event of interest. When the test signal is electromagnetically coupled to the test sample, the dielectric properties of the molecule or binding event modulate the test signal and produce a unique signal response. The signal response can be recovered and stored and can be used to detect and identify the molecules in other test samples. Additionally, interactions of other molecules with the first molecule (e.g., molecular binding) can be detected, as the test signal is further modified by the interaction of the second molecule with the first.

Test System Architecture

FIG. 1 illustrates a test set 100 configured to detect molecular events within a test sample in accordance with one embodiment of the present invention. The test system 100 includes a computer 105, a signal analyzer 110, and a resonant test assembly 120. Computer 105 controls the settings and operation of signal analyzer 110 via a command bus 107 (a general purpose instrument bus in one embodiment). Responsive to the computer's instructions, signal analyzer 110 transmits an incident signal 111 along a signal path 112 (typically a coaxial cable) to the resonant test assembly 120. Within the resonant test assembly 120, a resonant test structure 122 is positioned proximate to a volume of sample 130, such that the 122 is electromagnetically coupled (either directly or indirectly, as defined above) to molecular events occurring within the sample 130. As defined above, molecular events includes structural properties of proteins 132 as well as binding events 134. As the incident signal 111 illuminates the sample 130, the dielectric properties of the molecular events (132 or 134) modulate the incident signal 111. At least a portion of the modulated incident signal is reflected back toward and is recovered by the resonant test structure 122. The incident and reflected signals 111 and 113 are subsequently analyzed to calculate the measured permittivity of the molecular events.

Computer 105 may be any of a variety of commercially available computers such as series HP Vectra or HP 9000 available from the Hewlett Packard Company (Palo Alto, Cailf.). Others computation machines such as Macintosh or Unix-based machines may be employed in alternative embodiments. In a specific embodiment, computer 105 will include a graphical user interface such as LabView available from National Instruments (Austin, Tex.).

Figure 2A:
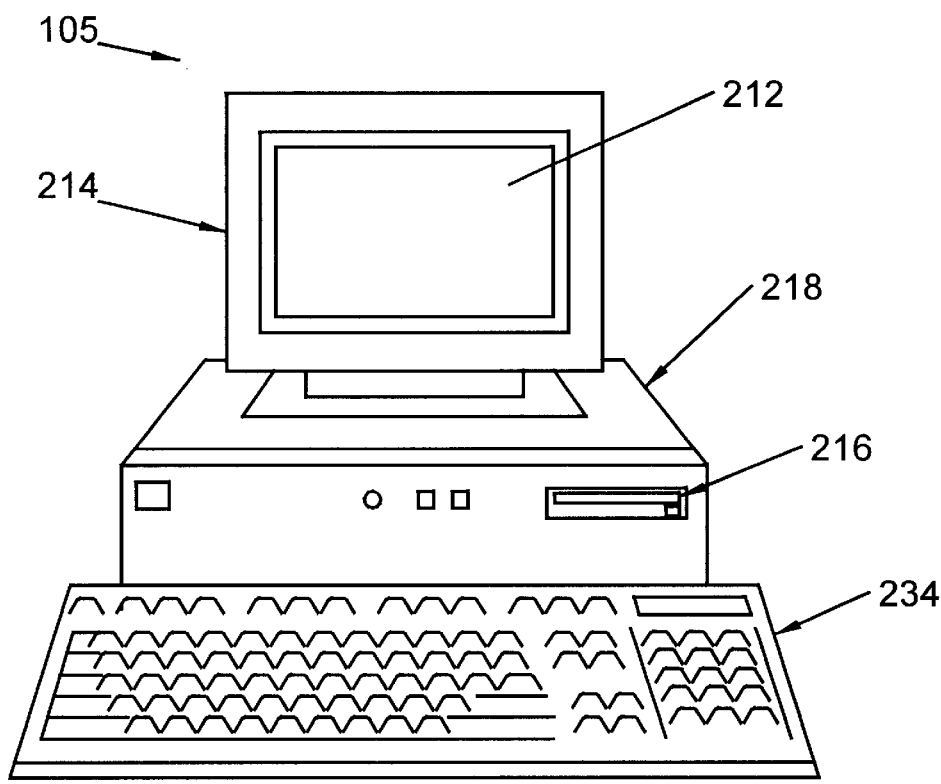
FIG. 2A illustrates a simplified block diagram of a computer system shown in FIG. 1 in accordance with the present invention.

FIG. 2A illustrates a simplified block diagram of the computer system 105 operable to execute a software program designed to perform each of the methods described herein. The computer system 105 includes a monitor 214, screen 212, cabinet 218, and keyboard 234. A mouse (not shown), light pen, or other I/O interface, such as virtual reality interfaces can also be included for providing I/O commands. Cabinet 218 houses a CD/DVD-ROM/R/RW drive 216, a hard drive (not shown), or other storage data mediums which can be utilized to store and retrieve digital data and software programs incorporating the present method, and the like. Although drive 216 is shown as the removable media, other removable tangible media including floppy disks, tape, and flash memory can be utilized. Cabinet 218 also houses familiar computer components (not shown) such as a processor, memory, and the like.

Figure 2B:
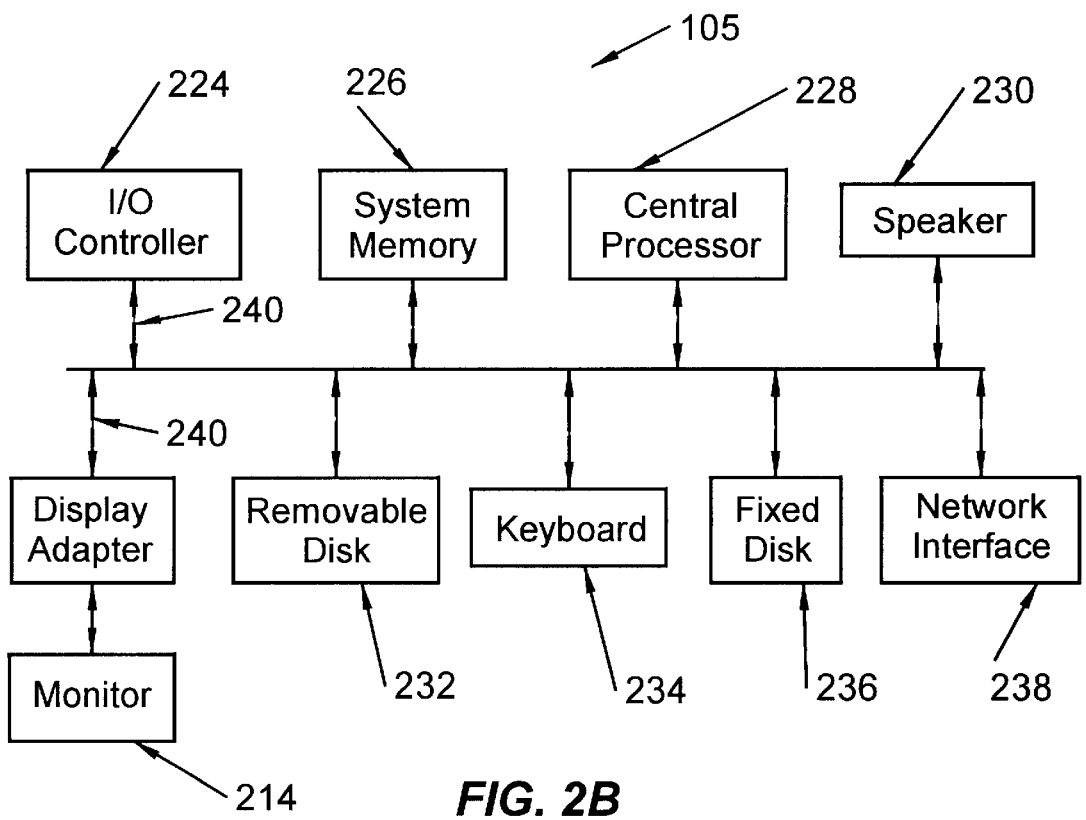
FIG. 2B illustrates the internal architecture of the computer system shown in FIG. 1.

FIG. 2B illustrates the internal architecture of the computer system 105. The computer system 105 includes monitor 214 which optionally is interactive with the I/O controller 224. Computer system 210 further includes subsystems such as system memory 226, central processor 228, speaker 230, removable disk 232, keyboard 234, fixed disk 236, and network interface 238. Other computer systems suitable for use with the described method can include additional or fewer subsystems. For example, another computer system could include more than one processor 228 (i.e., a multi-processor system) for processing the digital data. Arrows such as 240 represent the system bus architecture of computer system 210. However, these arrows 240 are illustrative of any interconnection scheme serving to link the subsystems. For example, a local bus could be utilized to connect the central processor 228 to the system memory 226. Computer system 105 shown in FIG. 2 is but an example of a computer system suitable for use with the present invention. Other configurations of subsystems suitable for use with the present invention will be readily apparent to of skill in the art.

Referring again to FIG. 1, signal analyzer 110 is operable to transit and receive the incident and reflected signals 111 and 113, respectively. Signal analyzer 110 may consist of any of a variety of commercially available instruments operable to transmit, receive, and measure the amplitude and/or phase of signals. In a specific embodiment, signal analyzer 110 is a vector network analyzer model number 8722 manufactured by Agilent Technologies (formerly Hewlett Packard Company, Palo Alto, Calif.). In alternative embodiments, the signal analyzer may be a scalar network analyzer, a vector voltmeter, or other instrumentation capable of providing amplitude or amplitude and phase information of incident and reflected signals.

Figure 3A:
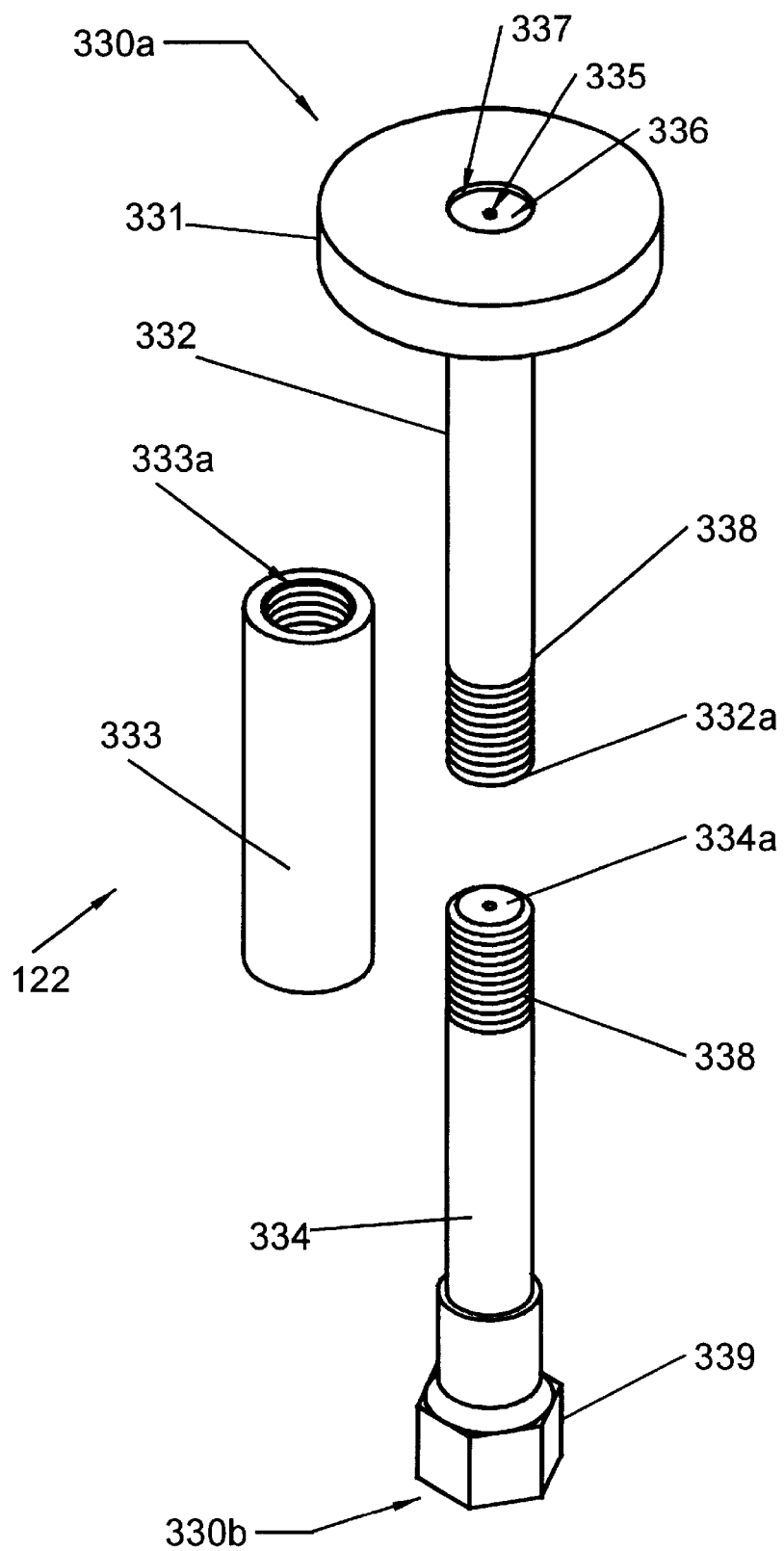
FIG. 3A illustrates, in accordance with the present invention, one embodiment of a resonant test structure shown in FIG. 1.

FIG. 3A illustrates one embodiment of a resonant test structure 122 (hereinafter "resonator") in accordance with the present invention. A specific embodiment is described in greater detail in applicant's commonly owned, co-pending patent application Ser. No. 09/687,456 entitled: "System and Method for Detecting and Identifying Molecular Events in a Test Sample," which is incorporated herein by reference.

As shown in FIG. 3A, the resonator 122 has two ports: a probe head 330*a* and a connecting end 330*b*. In a specific embodiment, the probe head 330*a* is an open-end coaxial cross section and the connecting end 330*b* is a coaxial-type connector, one embodiment of which is a SMA connector. Those of skill in the art will appreciate that other terminations (such as shorted or load terminations), as well as other circuit architectures (such as microstrip, stripline, coplanar waveguide, slot line, waveguide, etc.) can be used in alternative embodiments of the 122.

The resonator 122 further includes two coaxial sections 332 and 334, each having a center conductor 335, a dielectric insulator 336 (air in a specific embodiment), and an outer conductor 337 (typically used to provide a ground potential reference). The first section 332 consists of the aforementioned probe head 330*a* and a first gap end 332*a* located opposite thereto, each realized as an open-end cross section of the coaxial cable. A shelf (preferably conductive) 331 is attached flush (preferably via solder, conductive epoxy or other conductive attachment means) with the outer conductor 337 of the probe head 330*a*.

The second section 334 is of similar construction as the first section 332, having a dielectric insulator located between center and outer conductor. The second section 334 further includes a second gap end 334a and a connecting end 330b located opposite thereto. The second gap end 334a is realized as an open-end cross-section of the coaxial cable. The connecting end 330b is realized as a connector (SMA-type in a specific embodiment) operable to connect to the molecular detection system, further illustrated and described below. In a specific embodiment, the first and second sections 332 and 334 are each of the same dimensions as RG401 type semi-rigid coaxial cable, although larger or smaller diameter cables can be used as well. The length of the first section 332 is calculated to be approximately one-half wavelength in length at the desired frequency of resonance.

In a specific embodiment of the invention, the resonator 122 includes a tuning element 333 which is adjustably engaged between the first and second gap ends 332a and 334a to provide a variable gap distance therebetween. The gap provides a capacitive effect between the first and second sections 332 and 334, and it, in combination with the electrical length of the first section 332, is designed to provide a resonant signal response when the resonator 122 illuminates the sample. The tuning element 333 can be rotated to expand or contract the gap (and according, decreasing or increasing the value of the capacitive effect) between the first and second sections 332 and 334, thereby changing the resonant frequency of the resonator 122 to the desired frequency.

The tuning element 333 is preferably a hollow tube constructed from a material (stainless steel in one embodiment) that exhibits relatively high conductively to maintain ground potential between the first and second sections at the test frequency of operation. Further, the tuning element can include internal threads 333a which mate with external threads 338 disposed on the outer conductors of the first and second sections near the first and second gap ends 332a and 334a. In alternative embodiments of the invention, the tuning element 333 can be omitted, in which case the first and second sections 332 and 334 can comprise one continuous coaxial transmission line structure. The design of resonator 122 is described in greater detail in applicant's co-pending, patent applicant Ser. No. 09/687,456 entitled: "System and Method for Detecting and Identifying Molecular Events in a Test Sample," incorporated herein by reference.

Figure 3B:
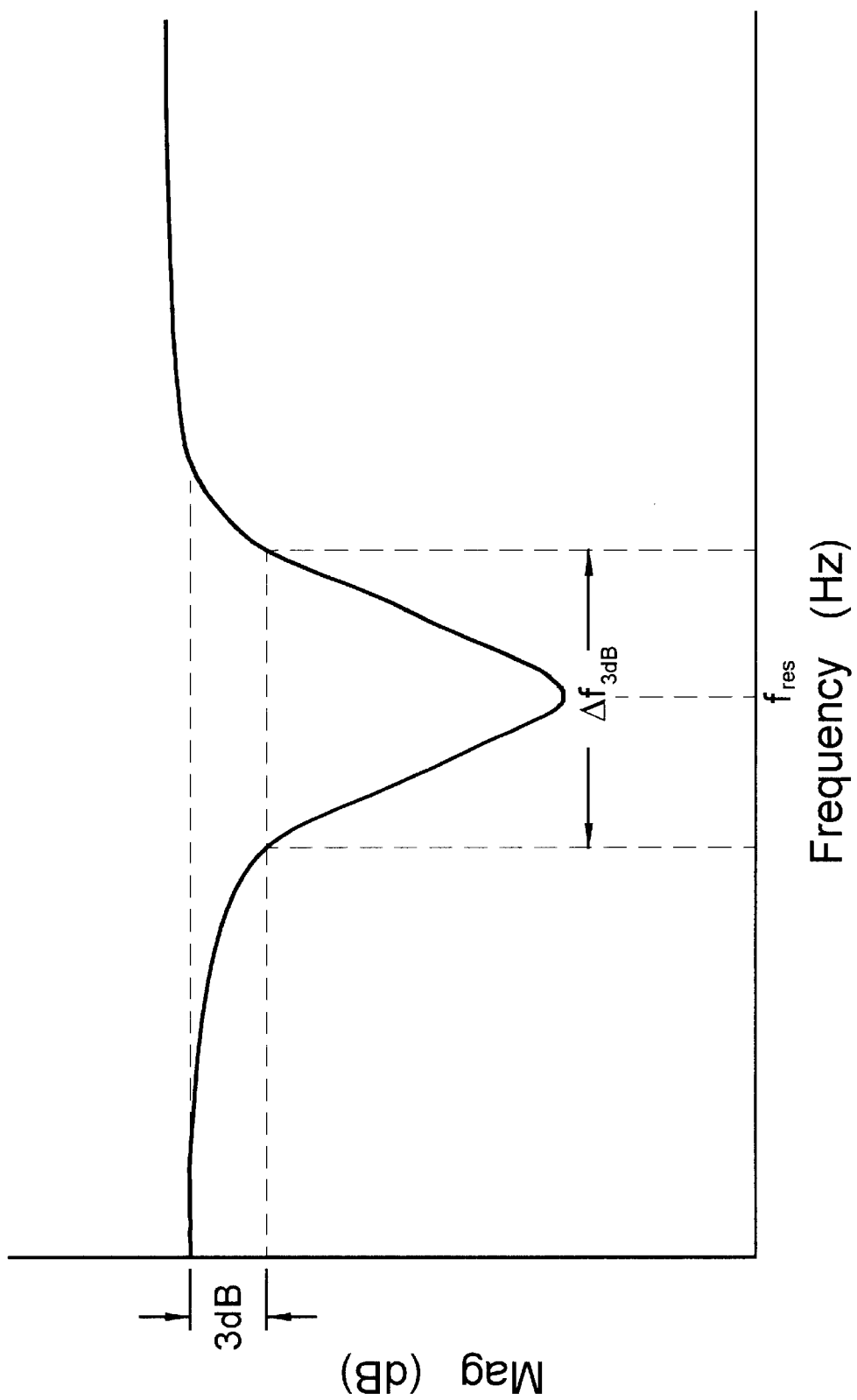
FIG. 3B illustrates, in accordance with the present invention, a second embodiment of a resonant test structure shown in FIG. 1.

FIG. 3B illustrates an exemplary s-parameter one-port return loss response (referred to as a $S_{11}$ response) obtained using the resonator 122. The response is characterized by an amplitude response (y-axis) extending over one or more frequencies (x-axis). As illustrated, the response exhibits a minimum amplitude at a frequency $f_{res}$ typically referred to as the resonant frequency of the resonator. At this frequency, signal power will be substantially retained within the resonator. This is the frequency at which the resonator is most sensitive since little power escapes from the resonator itself. A parameter referred to as the "Quality" or "Q"-factor is used to measure how well the resonator (or any resonant structure) retains signal power at its resonant frequency. Generally, the Q-factor is a ratio of the energy stored versus the energy dissipated at the resonant frequency $f_{res}$. Mathematically, the Q-factor can be expressed as $$Q = f_{res}/\Delta f_{3\,dB} \quad (1)$$

where:

$f_{res}$ is the frequency at which the amplitude of the return loss ($S_{11}$) reaches a minimum point; and $\Delta f_{3\,dB}$ is the $-3$ dB or half power bandwidth of the resonator above and below $f_{res}$ When the resonator 122 is electromagnetically coupled to the sample, the resonant frequency parameter $f_{res}$ is highly correlated to the real part of the sample's complex permittivity (dielectric constant), and the Q-factor is highly correlated to the imaginary part (dissipative loss). Measurement of these two quantities provides an accurate basis by which to detect and identify molecular events within the sample, although in alternative embodiments, one of the parameters may be sufficient.

As can be seen in FIG. 3B, the smaller the half-power bandwidth around the resonant frequency point $f_{res}$, the higher the quality (i.e., lower dissipative loss) of the resonator. In a specific embodiment, the resonator 122 exhibits a $f_{res}$ between 1 GHz and 1.5 GHz and an unloaded Q-factor of at least 200. While the resonant frequency $f_{res}$ and Q-factor can be easily obtained from the aforementioned $S_{11}$ plot, those skilled in the art of high frequency circuit design will understand that these quantities can be obtained from other s-parameter measurements (e.g., a two-port $S_{21}$ measurement), as well as from g-, h-, y- or z-parameter measurements, smith chart plots, and the like. An exemplary process of converting an $S_{11}$ response to the aforementioned $f_{res}$ and Q parameters is further described in FIG. 5C.

Figure 4A:
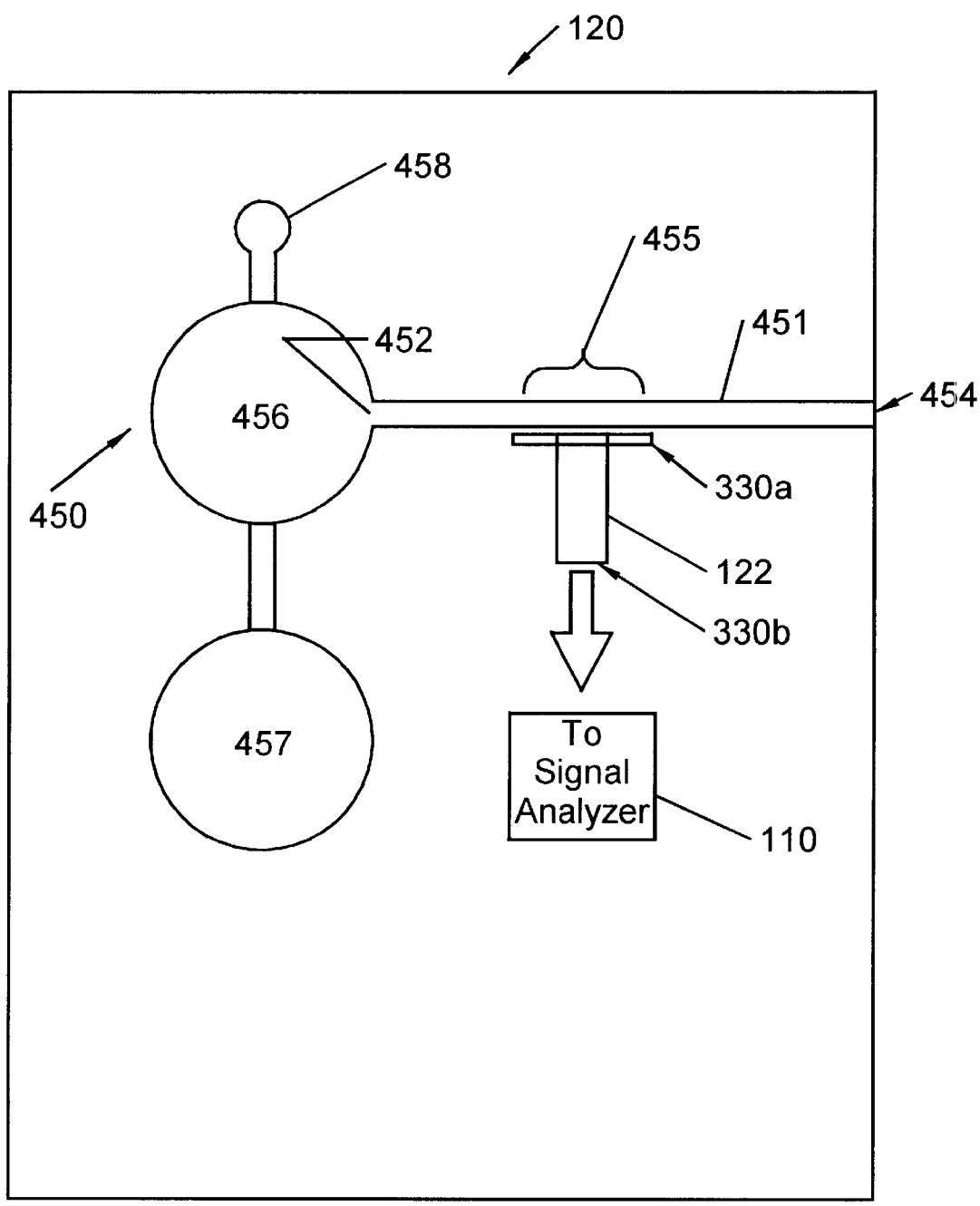
FIG. 4A illustrates a first embodiment of a resonant test assembly in accordance with the present invention.

FIG. 4A illustrates one embodiment of the resonant test assembly 120. In this embodiment, the resonant test assembly 120 includes a fluid transport system 450 integrated with a resonator 122. One embodiment of the 120 is described in greater detail in applicant's commonly-owned, co-pending patent application Ser. No. 09/678,456 entitled "System and Method for Detecting and Identifying Molecular Events in a Test Sample."

The sample transport system 450 includes a fluid channel 451, with a entry end 452 and an exit end 454. Motion of the test sample through the channel 451 is controlled by a fluid controller 456, which acts to move the test sample through the channel at times and under conditions selected by the user. Optionally, reservoir 458 can include a second analyte or test sample that can be mixed with the test sample stored in reservoir 457 as they are being introduced to the fluid channel 451. The ability to mix two test samples in close proximity to the detector makes it easy for the kinetics of binding events to be determined from this type of data. The fluid controller 456 can move the test sample in one direction, in forward and reverse directions, or pause the test sample for a predetermined duration, for instance, over the detection region in order to improve sensitivity.

The resonator 122 includes probe head 330a and connecting end 330b. The probe head 330a is positioned proximate to the detection region 455 of the fluid channel 451 and is operable to electromagnetically couple (directly or indirectly, as defined above) the incident test signal to the sample flowing through the detection region 455. The sample modulates the incident signal, a portion of which is reflected to the probe head 330a. The reflected modulated signal is subsequently recovered by the probe head 330a. The connecting end 330b is electrically connected (directly or via intervening components or circuitry) to the signal analyzer 110. In a specific embodiment in which the resonator 122 is a coaxial-type structure, the connecting end 330b can be a coaxial cable which extends from the signal analyzer, a compatible coaxial type connector such as a SMA-type connector, or other connector type familiar to those skilled in the art of high frequency measurement. In alternative embodiments of the invention in which a different type of resonator architecture is used (i.e., coplanar waveguide, microstrip, etc.), the connection port can comprise a compatible connection to provide signal communication to the permittivity test set.

Figure 4B:
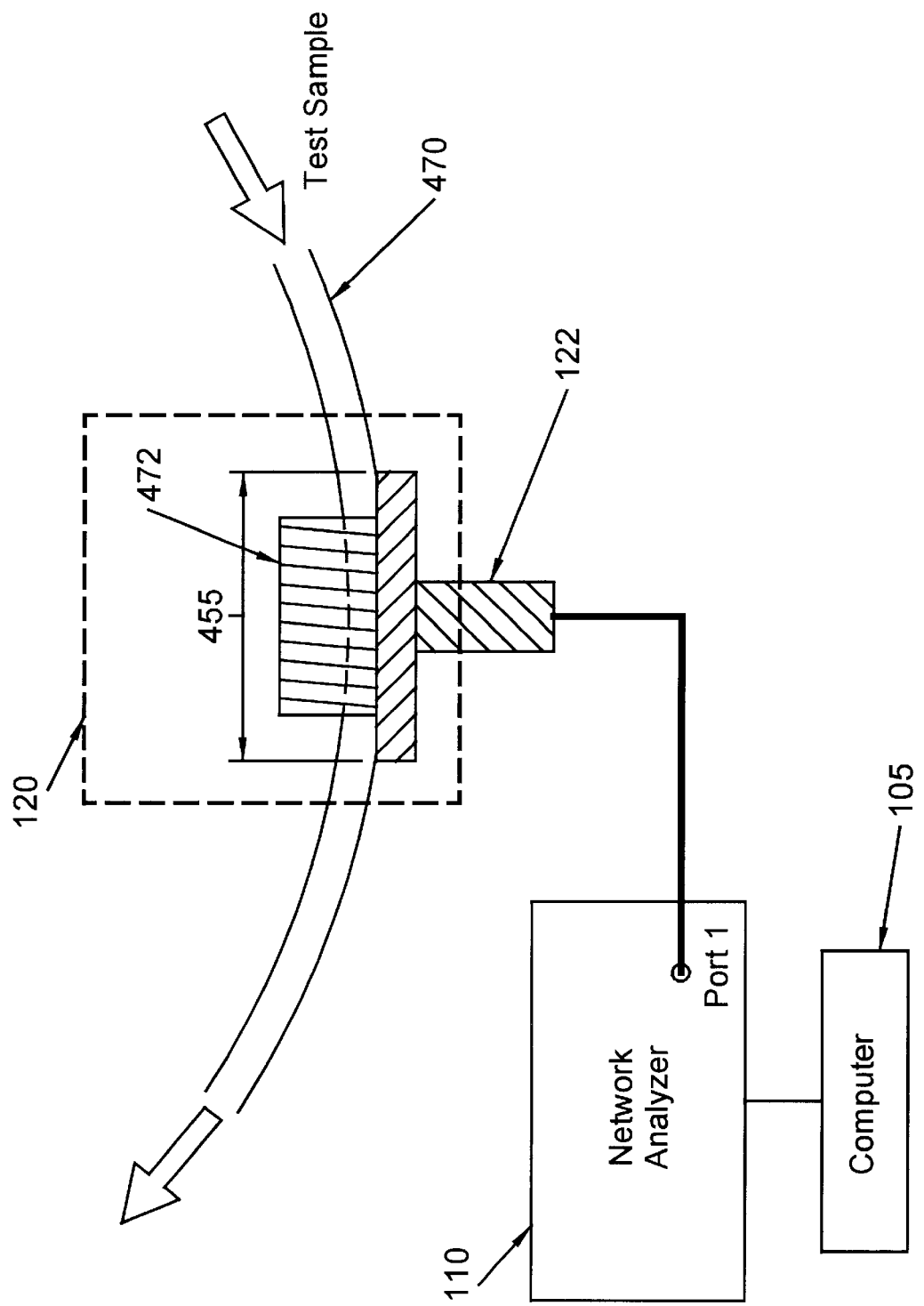
FIG. 4B illustrates a second embodiment of a resonant test assembly in accordance with the present invention.

FIG. 4B illustrates a second embodiment of the resonant test assembly 120. In this embodiment, the assembly 120 includes a length of RF permeable tubing 470, one example being PTFE type-tube available from Cole-Parmer Instrument Company (Vernon Hills, Ill.). The tubing 470 transports the test sample to the detection region 455 illuminated by the resonator 122. A cover piece 472, which is preferably constructed from a conductive material, includes a grooved portion through which tubing 470 extends.

In the illustrated embodiments of FIG. 4A and 4B, the probe head 330a is indirectly coupled (as defined above) to the sample by closely positioning the probe head proximate to the sample. The intervening material(s) that physically separates the probe head 330a from the test sample can include solid phase materials, such as PTFE, alumina, glass, sapphire, diamond, Lexan®, polyimide, or other dielectric materials used in the area of high frequency circuit design; materials used in the fabrication of microfluidic devices or semiconductor processing; or other known materials which exhibit a relatively high degree of signal transparency (i.e., low dielectric loss tangent) at the desired frequency of operation. In a specific embodiment, the intervening material can be an electrically insulating material, some examples of which are described above. Alternatively or in addition, liquid and/or gaseous phase materials (including air) that exhibit a relatively high degree of test signal transparency can also comprise the intervening materials.

The thickness and dielectric properties of the intervening materials can vary depending upon the type of fluidic system implemented and the resonator used. For instance, in systems in which the separation distance is great, a low dielectric loss tangent ($10^{-3}$, $10^{-4}$, $10^{-5}$, $10^{-6}$ or lower), high dielectric material (greater than 3) is preferred to provide maximum coupling between the test sample and the resonator 122. In systems in which the separation distance is relatively short, materials of higher loss tangents and/or lower dielectric constant can be tolerated. In a specific embodiment, the tubing 470 is a section of PTFE tube having cross-section dimensions of 0.031 inch I.D., 0.063 inch O.D., wall thickness 0.016 inch. The dielectric constant of PTFE is approximately 2, and the dielectric loss tangent generally $3 \times 10^{-4}$. The separation distance is approximately the tube's wall thickness, about 0.016". In other detector assemblies, separation distances can be on the order of $10^{-1}$ m, $10^{-2}$ m, $10^{-3}$ m, $10^{-4}$ m, $10^{-5}$ m, or $10^{-6}$ m, and can be much smaller, e.g., on the order of $10^{-9}$ m to $10^{-12}$ m in some cases (such as in a channel etched into the surface of a substrate and having a metallic signal path element with a thin polymer layer on the test sample side acting as the fourth side of the channel). Decreasing the separation distance and loss tangent of the material, or increasing the dielectric constant of the material, the detection area 455, the sample volume, or analyte concentration will operate to increase detection sensitivity. The separation material, as illustrated above, can a solid phase material, or alternatively (or in addition) consist of a liquid or gaseous phase material or a combination thereof.

In an alternative embodiment, the probe head 330a and sample may be directly coupled (as defined above), in which case the sample comes into direct contact with the probe head 330a. In this embodiment, measurement sensitivity is increased as the signal loss contributed by the intervening material is not present. This embodiment may be realized in a variety of ways, for instance in FIG. 4A or 4B by extending the center conductor 335 such that it contacts the sample moving through the detector region 455 of the fluid channel 451. In such an embodiment, the channel substrate (the material on which the fluid channel 451 is formed) may include a cavity within the detector region 455 for receiving the center conductor 335. The dielectric properties of the channel substrate may be used as the dielectric material and the outer conductor of the resonator extended to maintain the characteristic impedance of the resonator (typically 50 ohms). Alternative realizations in which the sample contacts the probe head 330a will be readily apparent to those skilled in the art.

Figure 5A:
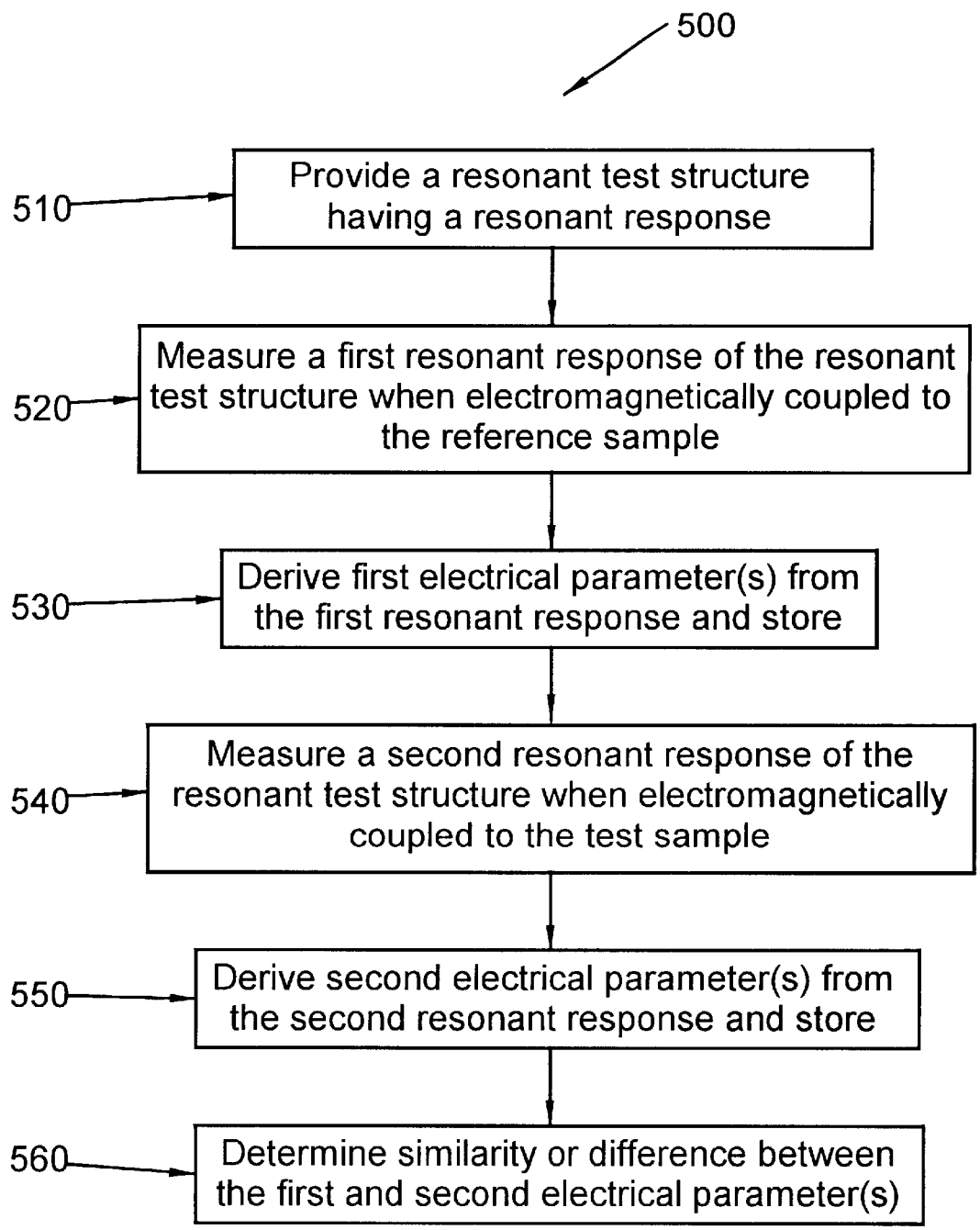
FIG. 5A illustrates a method for detecting and identifying molecular events in a sample using a resonant test structure in accordance with the present invention.

FIG. 5A illustrates a method for detecting and identifying molecular events in a sample using a resonant test structure (referred to as a "resonator") in accordance with the present invention. At 510, resonator configured to output a resonant response is provided. In a specific embodiment, the resonator is a one-port coaxial resonant probe, an example of which is shown in FIG. 3A. The present invention is not limited to a coaxial resonator, and other distributed or lumped element resonant circuits and structures may be used in alternative embodiments. Some examples include resonant cavities, openshort circuited transmission line structures, quarter wavelength or other periodic structures, filters, ring or dielectric resonators, or other similar structures in both planar and non-planar topologies. The resonator is not limited to passive circuits or structures. Active circuits such as amplifiers, active filters, or oscillators may be used to further enhance, or itself provide the resonant response.

The resonant response is the measurable signal response of the resonator when a test signal is input and an output signal is recovered. In the illustrated embodiment, the resonant response consists of an input return loss ($S_{11}$) response. Those of skill in the art of resonant electromagnetic circuits and structures will appreciate other measurements may also be used in alternative embodiment including multiple-port s-parameter measurements, g-, h-, y- or z-parameter measurements to name a few.

At 520, a first resonant response of the resonator is measured when the test structure is electromagnetically coupled to the reference sample. In an exemplary embodiment, the resonant response measured is an input return loss (or $S_{11}$) response of the resonator 122 obtained using a computer-controlled vector network analyzer, as illustrated in FIG. 1. The composition of the reference sample is known and will depend on the measurement being made (i.e., on the molecular event being detected) but typically consists of all the components of the test sample save one. For example, the reference sample can consist of a buffer and the first of two components suspected of binding to each other, while the test sample consists of the same buffer and first component, but now also contains the second of the two suspected binding partners. Since the assay can be carried out on a variety of samples, the actual components present in the reference sample (and the corresponding test sample) can vary widely. For example, the reference sample can consist of the native environment in which the molecular structure (or one component of a binding event) resides, such as cellular lysate. Alternatively, a reference sample can be a simpler system, such as a buffer only, a buffer that contains a purified protein, a mixture of proteins, or a mixture of proteins or an individual protein and non-proteinaceous components, such as co-factors and/or binding assistants. Those skilled in the art will appreciate that the foregoing examples are only illustrative, and other compositions are possible. In an exemplary embodiment, the reference sample is indirectly coupled to the resonator via a PTFE tube as shown in FIG. 4B. In other embodiments, the reference sample is supplied using microfluidics or another fluid transport system and is directly coupled to the resonator.

In the preferred embodiment, the reference solution is removed and the test sample is supplied to the detection region while the test system remains substantially undisturbed. Transportation of the each sample may performed using one or more small volume plugs (e.g., 5 μl) preceded and/or followed by a main sample plug of greater volume (e.g., 15 μl). The shorter duration sample plugs operate to insulate the main plug from changes in concentration. Air plugs can also be introduced as the spacer material, before and/or after the sample plugs to further minimize mixing of fluids or changes in their concentration. Air plugs can also be used as indicators to inform the test system (or operator) of the test sample's position within the fluid channel. A detergent may be used between the reference and test sample plugs to remove any residue of the previous sample. Other transporting techniques are described in applicant's commonly-owned, co-pending patent application Ser. No. 09/687,456, entitled "System and Method for Detecting Molecular Events in a Test Sample."

Next at 530, one or more first electrical parameters are derived from the first resonant response. This derivation process is further illustrated in FIG. 5C below may be performed using an automated test system, such as an automated network analyzer or a computer system similar to that shown in FIGS. 2A and 2B. In the exemplary embodiment, the derived electrical parameters are the resonant frequency $f_{res}$ and Q-factor, although other electrical parameters may be used in other embodiments. The parameters are subsequently stored for later retrieval and comparison, as further illustrated below.

At 540, a second resonant response of the test structure is measured when the is electromagnetically coupled to the test sample and at 550, one or more second electrical parameters are derived from the second resonant response. The second electrical parameters are subsequently stored for later retrieval and comparison with the first electrical parameters, as will be further illustrated below. In the preferred embodiment, the first and second resonant responses are of the same type (input s-parameters in the illustrated embodiment), although in an alternative embodiment diverse resonant responses may be obtained and converted to electrical parameters of the same type.

At 560, the first and second electrical parameter(s) are compared for similarities or differences to determine the presence or absence of molecular events within the test sample. If the computed difference does not exceed a predefined threshold, identity between the test and reference samples is indicated. In this instance, if the reference sample includes a particular molecular event, the test sample is identified as containing the same molecular event. If the reference sample is known to be free of the particular molecular event, the test sample is also determined to exclude the particular molecular event.

If the difference exceeds the predefined threshold, the presence or absence of the molecular event may also be indicated depending upon the known composition of the reference sample. When the reference includes is known to be free of a particular. The comparison process 560 may be repeated one or more times where the test sample circuit parameters are compared to electrical parameters corresponding to a second reference sample, previously characterized. This process (further illustrated in FIG. 5D) is preferably performed using the computer system 105 illustrated in FIGS. 2A and 2B.

It will be apparent that the present methodology does not require a washing step in which the buffer or the non-reacting components of the test sample are removed from the detection region before a measurement is made. There is no requirement, for example, that two potential binding partners be separated from each other in order to distinguish a binding event from simple mixing in which binding does not occur. Of course, the methodology of the present invention can also be carried out after a washing step if desired for other reasons.

The absence of a washing step enables real-time detection and identification of molecular events in a samplet. The test signal may be launched and electromagnetically coupled to the sample during the application of the sample in order to observe the changes in the signal response which occur as a result of the binding event.

For example, a computer-controlled automated network analyzer can be configured to store the first resonant response corresponding to a reference sample, e.g., a buffer solution. A test sample containing the buffer, a protein, and ligand having a known or unknown binding affinity to the protein is supplied to the detector region of the resonant test assembly (the protein and ligand may possibly be supplied from two independent sources and mixed within the detector region). The computer-controlled network analyzer can be controlled to obtain the second resonant response produced as a result of the binding, convert the first and second responses to electrical parameters, e.g. $f_{res1}$ and $f_{res2}$, compute their difference $\Delta f_{res}$ and output the result all while the interaction is occurring. The result is a comparison between the binding event relative to the buffer. In other embodiments the reference sample may consist of other components, such as the buffer and either the protein or the ligand alone. As the reader will appreciate, this real-time measurement application is quite advantageous not only in the detection and identification of molecular structures and binding events, but also in determining the kinetics of molecular interactions as well.

Figure 5B:
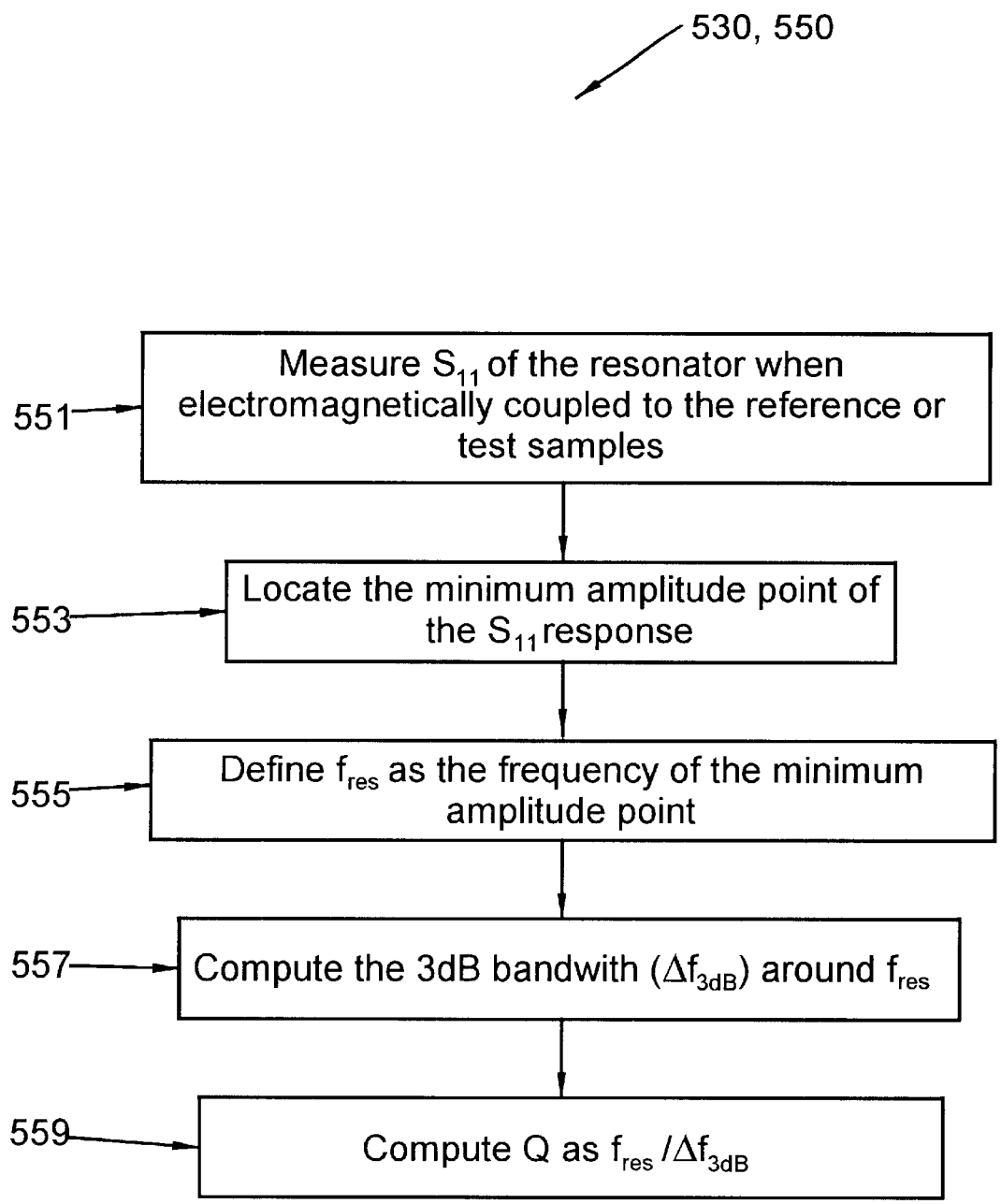
FIG. 5B illustrates a method for converting an $S_{11}$ response into resonant frequency and Q-factor parameters in accordance with the present invention.

FIG. 5B illustrates one embodiment of processes 530 and 550 in which electrical parameters Q and $f_{res}$ are derived from the resonant $S_{11}$ response. Initially at 551, the $S_{11}$ amplitude versus frequency response of the reference or test sample, respectively, is measured. This process is performed using the computer-controlled vector network analyzer shown in FIG. 1.

Next at 553, the minimum amplitude point of the $S_{11}$ response is located. This process can be performed using one of the pre-programmed function keys of an automated network analyzer. The frequency point at which the amplitude minimum is located is defined as the resonant frequency $f_{res}$ of the resonator (process 555).

At 557, the 3 dB bandwidth ($\Delta f_3$ dB) around the resonant frequency $f_{res}$ is computed. This process is performed by first locating the two frequencies at which the resonant response is −3 dB below the nominal, non-resonant response as illustrated in FIG. 3B. Next, the bandwidth between the selected frequencies are computed. The automated network analyzer may be pre-programmed to locate the −3 dB frequency points and to compute the resulting 3 dB bandwidth. At 559, the Q-factor is computed as the quotient of the resonant frequency $f_{res}$ and the 3 dB bandwidth $\Delta f_{3\,dB}$. This computation may be made by the computer system illustrated in FIGS. 2A and 2B.

In an alternative embodiment, the frequency and Q-factor can be obtained by curve-fitting the Lorentzen expression for the resonant response to the measured resonant response. Equation (2) is the Lorentzen expression for the response of a resonant structure:

$$|S_{11}| = \{[Q^2(f_{meas}-f_{res})^2]/[f_{res}^2 + Q^2(f_{meas}-f_{res})^2]\}^{1/2} \qquad (2)$$

where:

Q is the Q-factor of the resonator;

$f_{res}$ is the resonant frequency of the resonator; and $f_{meas}$ is the frequency at which the $S_{11}$ response is taken;

Once the Lorentzen expression is curve-fit to the magnitude of the input return loss, the resonant frequency $f_{res}$ and Q-factor Q can extracted. In a particular embodiment, the test system includes a computer system which executes a curve-fitting program (Labview® platform in one embodiment) to extract the resonant frequency and Q-factor values from the measured s-parameters.

Figure 5C:
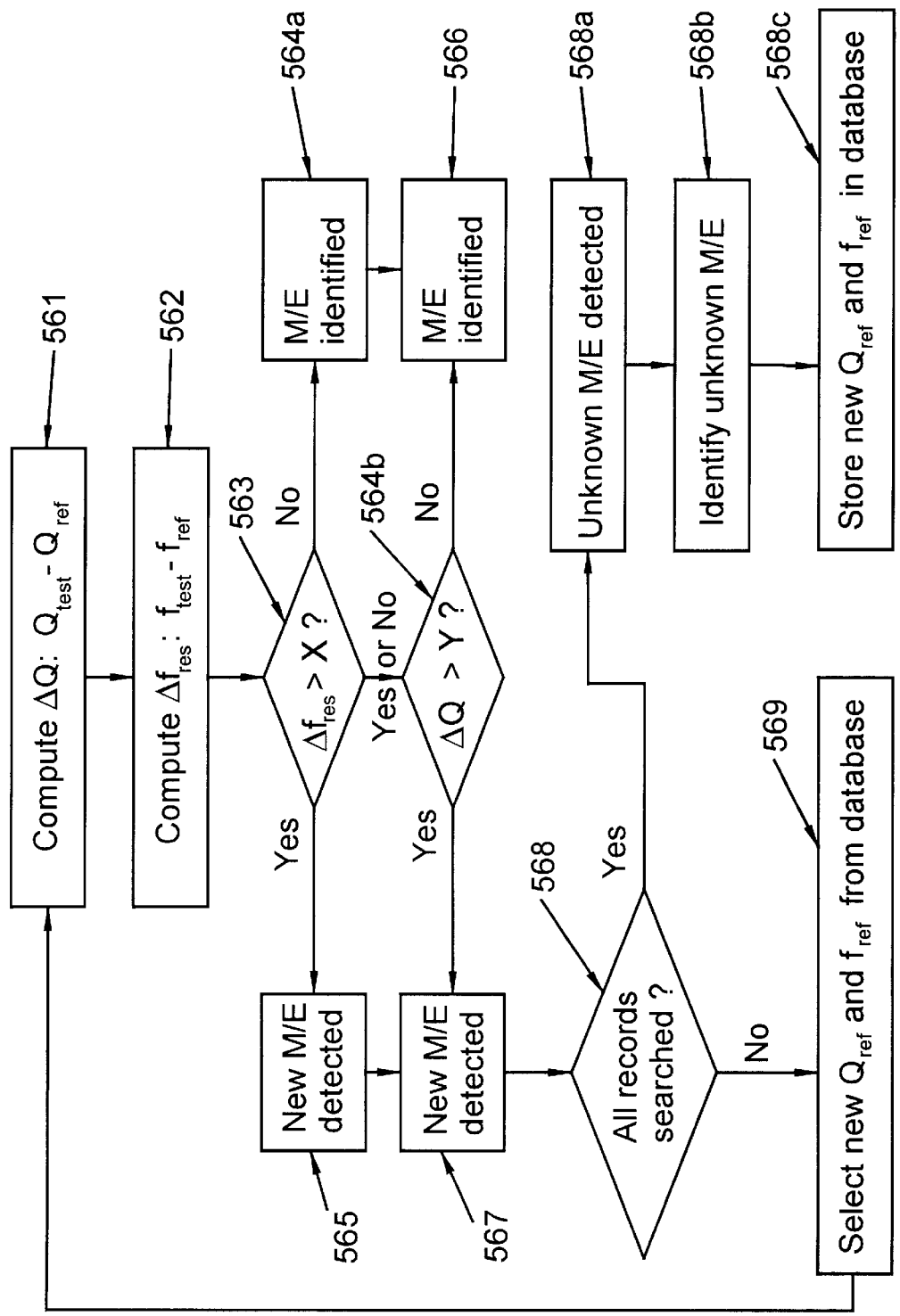
FIG. 5C illustrates a method for comparing the resonant frequency and Q-factor parameters in accordance with one embodiment of the present-invention.

FIG. 5C illustrates one embodiment of the process 560 in which the first and second electrical parameters are compared. The following example is one in which the reference sample includes a known molecular event for which the test sample is interrogated. As noted above, an alternative embodiment of the present invention may employ a reference sample known to exclude a particular molecular event to determine if the test sample similarly excludes the molecular event.

Initially at 561, a change in Q-factor ($\Delta Q$) is computed by subtracting the reference sample Q-factor from the test sample Q-factor. At 562, a change in the resonant frequency ($\Delta f_{res}$) is computed by subtracting the reference sample resonant frequency from the test sample resonant frequency.

At 563, a determination is made as to whether the change in the resonant frequency ($\Delta f_{res}$) exceeds a predefined value X, ±1 KHz in the illustrated embodiment. The 1 KHz value was chosen based upon the resonator's resonant frequency, q-factor, and the test system's sensitivity and measurement accuracy. The reader will appreciate that other values for $f_{res}$ (or another electrical parameter used) may be used in an alternative embodiment. For instance, the threshold may be computed as a percentage of the average value of the difference quantities, e.g., 0.5%, 1%, 2.5%, 5%, 7.5%, 10% of $\Delta f$ (or $\Delta Q$) would serve as each's threshold value.

If at 563, the computed $\Delta f_{res}$ does not exceed the predefined value X, the molecular event (M/E) in the test sample is identified as that contained within the reference sample (process 564a). Alternatively, the match is not deemed conclusive and a secondary inquiry is made at 564b to determine if the computed $\Delta Q$ exceeds a predefined threshold, ±5 in the illustrated embodiment. This value was chosen based upon the resonator's resonant frequency, q-factor, and the test system's sensitivity and measurement accuracy. The reader will appreciate that other values for Q (or another electrical parameter used) may be used in an alternative embodiment, as described in the previous paragraph. While the exemplary embodiment illustrates the characterization of molecular events using two parameters ($f_{res}$ and Q-factor), additional quantities (such as pH, temperature, etc.) may be used to further characterize molecular events in order to provide a greater degree of specificity and differentiation between reference and test sample molecular events.

If at 563, the computed $\Delta f_{res}$ exceeds the predefined value X, the molecular event in the test sample is identified as a new molecular event at 565. In an alternative embodiment, detection of a new molecular event is not deemed conclusive at 565, and the process continues at 564b where a secondary inquiry is made to determine if $\Delta Q$ exceeds the predefined value Y. If it does, a new molecular event is deemed identified at 567. If at 564b, $\Delta Q$ does not exceed the predefined value Y, the molecular event is identified as that contained within the reference sample.

If a new molecular event (relative to the reference sample) is detected at 565 or 567, the illustrated process attempts to identify the new molecular event. In a specific embodiment, this process includes searching a database containing database records, each database record corresponding to a reference sample having measured $f_{ref}$ and $Q_{ref}$ values associated therewith. The reference sample database preferably stores a multitude of database records representing a variety of reference samples. In addition to the aforementioned $f_{ref}$ and $Q_{ref}$ values, each reference sample database record may further include a variety of sample and/or test system conditions, for example, sample temperature, sample pH, input, signal power, resonator's architecture, to name a few. The reference sample database is preferably stored in memory (electronically, or on one or more fixed or removable disks) of the computer system shown in FIGS. 2A and 2B.

The database searching process begins at 568 where an inquiry is made as to whether all of the database records have been searched. If not, the process continues at 569 where a new database record containing $f_{ref}$ and $Q_{ref}$ values for a new reference sample are retrieved. The retrieved $f_{ref}$ and $Q_{ref}$ values are used with the test sample $f_{test}$ and $Q_{test}$ values to compute the $\Delta f_{res}$ and $\Delta Q$ values. The processes of 563–568 until the molecular event is identified.

If after all of the database records have been accessed, none of the computed $\Delta f_{res}$ and $\Delta Q$ values are within the predefined range, an unknown molecular event, relative to the reference samples stored in the database, is identified (process 568a). At 568b, the molecular event (or absence thereof) is identified using conventional techniques such as nuclear magnetic resonance (NMR) spectroscopy, fluorescent labeling, and others as described herein. At 568c, a new reference sample database record of the newly identified molecular event is made. The new reference sample database record includes the name or other identifier of the molecular event, the computed $f_{ref}$ and $Q_{ref}$ values of the molecular event obtained in process 520 above, and any other sample or test system conditions, such as temperature, pH, input signal power, etc., as described above.

FIG. 6 illustrates an exemplary reference sample database 600 having database fields 610, 620, 630, 640, 650, 660, and 670 for storing specific portions of reference sample database records 601–605. Each database record includes a record identifier $610_i$, a molecular event identifier $620_i$, a test structure identifier $630_i$, a $Q_{ref}$ value $640_i$, a $f_{ref}$ value $650_i$, a signal input power value $660_i$, and a sample temperature value $670_i$, and each of the aforementioned identifiers and values $610_i$–$670_i$ are stored in their respective database fields 610–670. The illustrated database structure is exemplary and other identifiers and/or values corresponding to other sample or test system conditions may be included alternatively, or in addition to those shown.

The record identifier $610_i$ is data which uniquely identifies each of the database records. While shown as a four digit numeric code, the record identifier $610_i$ may be alphabetic or alphanumeric of arbitrary length. The molecular event identifier $620_i$ is data which identifies the subject molecular event in the reference sample. For example, database record 601 has a molecular event identifier of "BSA(PBS)" indicating the protein BSA in a PBS buffer solution, and database record 603 has a molecular event identifier of "HAS+SAL(DI)" indicating a binding event between human serum albumin and salbutamol in a de-ionized water buffer. The identifiers are shown as alphabetic/symbol, but other formats may be used in alternative embodiments.

The resonator identifier $630_i$ is data which identifies the resonator used to obtain the $Q_{ref}$ and $f_{ref}$ values. As an example, database record 601 has a resonator identifier of "Coax 003" symbolizing a coaxial resonator, version 3 as the test structure used for the measurement. Database records 602, 604, and 605 include "Cav," "Ring," and "Stub" indicating cavity, ring, and open (or short) circuited stub type resonators. The identifiers are shown as alphanumeric, although other formats may be used in alternative embodiments.

The $Q_{ref}$ value 640$_i$ is data representing the q-factor of the resonator when electromagnetically coupled to the reference sample. The $f_{ref}$ value 650$_i$ is data representing the resonant frequency of the resonator when electromagnetically coupled to the reference sample. The signal input power value 660$_i$ is data representing the amplitude of the incident test signal illuminating the sample. The sample temperature value 670$_i$ is data representing the temperature of the sample when the resonant response is measured. The identifiers are shown in numeric format, although other formats may be used in alternative embodiments.

Using the systems and methods of the present invention, several experiments were performed to detect and identify molecular events in a solution. The test system employed is substantially as illustrated in FIG. 1, and includes a vector network analyzer, a computer, a resonator, and a length of PTFE tube (Cole-Parmer Instrument Company of Vernon Hills, Ill.). The vector network analyzer used was model number HP 8714 manufactured by Agilent Technologies, Inc. (Palo Alto, Calif.) The computer is an HP Vectra computer (Hewlett Packard Company, Palo Alto, Calif.) executing a graphically user interface (LabView® platform) to control the operation of the network analyzer and to display the resulting data. The coaxial resonator 122 illustrated in FIG. 3A was used in the experiments to illuminate the reference and test samples. The resonator exhibited a resonant frequency $f_{res}$ of approximately 1 GHz when electromagnetically coupled to PTFE tube containing the reference sample. The PTFE tube 470 is used to transport the reference and test samples to the detection region of the resonant test assembly and measures 0.031" I.D., 0.063" O.D., wall 0.016" in cross-section dimensions.

The proteins used for the experiment included bovine serum albumin (BSA), ribonuclease (rnase), urease, myoglobin, fibrinogen (type I-S, bovine), chicken lysozyme (egg white), and turkey lysozyme. Phosphate buffer solution (PBS, pH 7.4) was purchased from Sigma (St. Louis, Mo.) and used as the reference sample.

In the reference measurement, PBS buffer was introduced into the tube and transported to the detection region, and a $S_{11}$ (return loss) measurement of the resonator was taken. In the illustrated example, the measurement was taken at 1 GHz over a 100 KHz band. From the measured $S_{11}$ response, the resonant frequency $f_{res}$ and Q-factor of the resonator were computed and stored, as described above.

Next, each of the aforementioned protein solutions were introduced into the tube and transported to the detection region. The resonator's $S_{11}$ response was measured (over the same frequency range as above) and the corresponding resonant frequency $f_{res}$ and Q-factor parameters derived therefrom. Subsequently, the difference in the resonant frequencies $\Delta f_{res}$ is computed. This quantity was subsequently plotted versus the resonator's measured Q-factor when electromagnetically coupled to the test sample. FIG. 6 illustrates this mapping.

Figure 7:
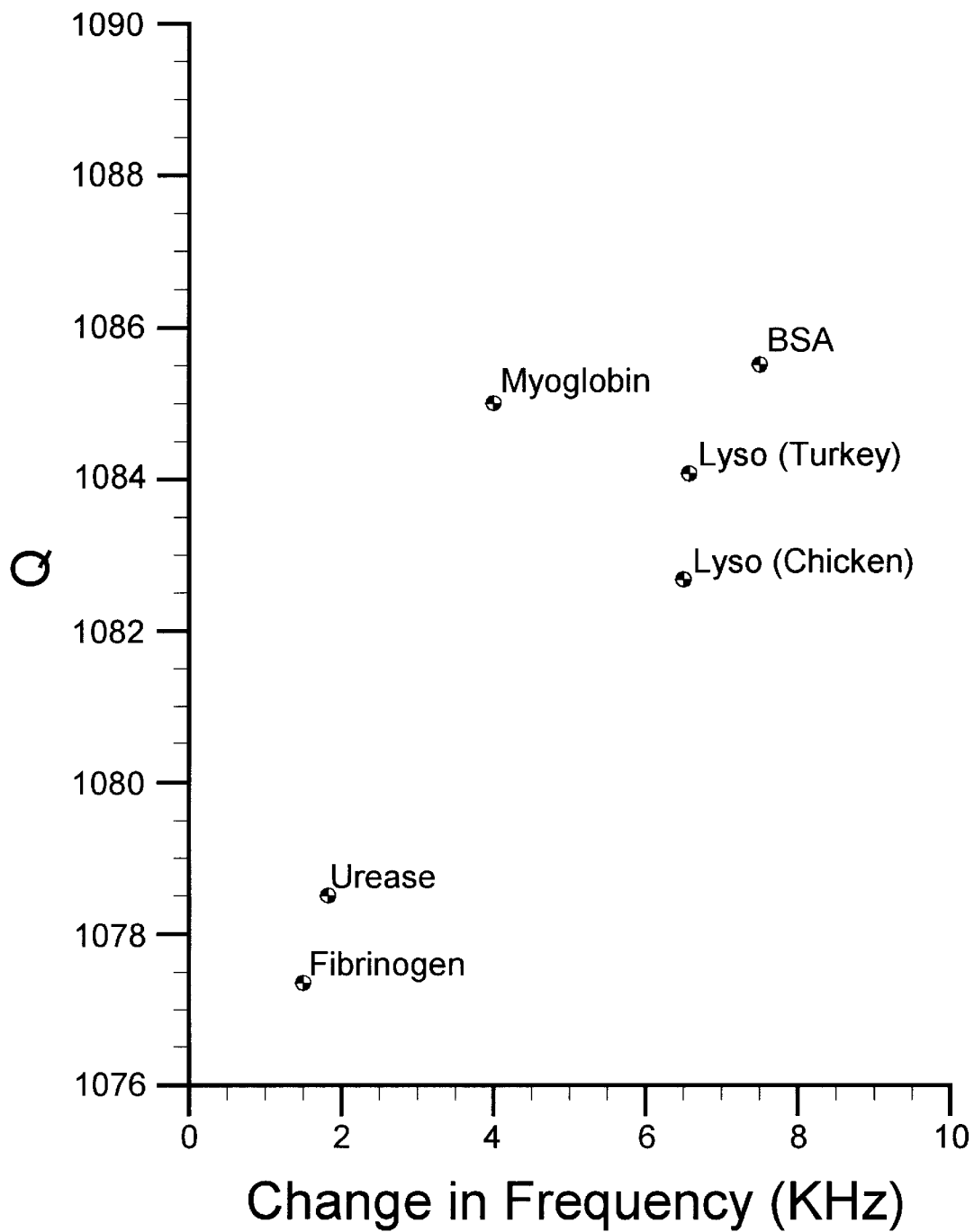
FIG. 7 illustrates a graph showing the q-factor versus a change in resonant frequency for different proteins in accordance with the present invention.

As illustrated in FIG. 7, the resonator exhibited a unique change in its resonant frequency (relative to the PBS buffer) for all of the protein solutions. Specifically, the resonator exhibited a change in its resonant frequency of approximately 1.75 KHz for fibrinogen, 2 KHz for urease, 4 KHz for myoglobin, 6.5 KHz for chicken lysozyme, 6.75 KHz for turkey lysozyme, and 7.5 KHz for BSA, using an input test signal of approximately 1 GHz. The difference in resonator Q-factors can be also used to distinguish between proteins, especially when the resonant frequency differences are small, as in the case of chicken and turkey lysozyme. A similar process can be performed in which the relative change in Q-factor is plotted versus the resonant frequency of the resonator when electromagnetically coupled to the protein (or buffer) solution. In still a further alternative embodiment, the relative change in the resonant frequency may be plotted versus the relative change in the Q-factor for each protein solution. The reader will appreciate that these are but a few of the possible permutations that may be used in the present invention.

Further, additional variables, such as temperature, pH, etc. may also be used to further characterize the protein solution or other molecular event. Characterizing the molecular event using additional variables is advantageous in that it permits the classification of a larger number of molecular events as well as providing a greater degree of differentiation therebetween. The later advantage is especially important in differentiating between structurally similar proteins, single nucleotide polymorphisms (SNPs), or similar bound and unbound molecular structures.

The reader will appreciate that the aforementioned data points (Q and $\Delta f_{res}$ in the above example) can be associated with its corresponding protein or molecular event and stored in a database for later retrieval and comparison to an unknown sample to identify the unknown sample's molecular events. A close correlation between the measured and stored data points would indicate that the unknown sample includes the molecular event corresponding to the stored data points. As noted above, each molecular event may be described by more than two data points to increase classification capacity of, and degree of differentiation between molecular events.

While the above is a complete description of possible embodiments of the invention, various alternatives, modifications, and equivalents can be used. For example, the resonator may be of a different circuit topology such as microstrip, coplanar waveguide, or suspended substrate, or non-TEM topologies, such as conductive or dielectric waveguide. Further, the system and method of the invention is not limited to the detection and identification of proteins but any molecular event as defined herein.

Applicant's commonly-owned U.S. patent application entitled "Bioassay Devices for Detecting Molecular Binding Events," Ser. No. 09/775,718 is concurrently filed herewith. The following commonly owned, co-pending patent applications, as well as all publications and patent documents recited in this application are incorporated by reference in their entirety for all purposes to the same extent as if each individual publication and patent document was so individually denoted:

Ser. No. 09/243,194, entitled: "Method and Apparatus for Detecting Molecular Binding Events," filed Feb. 1, 1999,
Ser. No. 09/365,578, entitled "Method and Apparatus for Detecting Molecular Binding Events," filed Aug. 2, 1999;
Ser. No. 09/365,978, entitled: "Test Systems and Sensors For Detecting Molecular Binding Events," filed Aug. 2, 1999; and
Ser. No. 09/687,456, entitled "System and Method for Detecting Molecular Events in a Test Sample," filed Oct. 13, 2000.

What is claimed is:

1. A method for detecting a molecular event in a test sample, the method comprising:
   providing a test structure having a measureable signal response when a test signal is input and an output signal is recovered, wherein the measureable signal response is a resonant response;
   obtaining a first resonant response of the test structure when the test structure is electromagnetically coupled to a reference sample;
   obtaining a second resonant response of the test structure when the test structure is electromagnetically coupled to the test sample;
   deriving one or more electrical parameters from the first resonant response;
   deriving one or more electrical parameters from the second resonant response;
   detecting similarity or difference between the electrical parameters derived from the first and second resonant responses as an indication of the molecular event in the test sample;
   determining the difference between the electrical parameters derived from the first and second resonant response; and
   indicating that, if the reference sample contains the molecular event and if the difference between the one or more electrical parameters derived from the first and second resonant responses does not exceed a predefined value, the test sample includes the molecular event.

2. The method of claim 1 wherein the one or more electrical parameters comprise s-parameter measurements, Q-factor measurements, or resonant frequency measurements.

3. The method of claim 1, wherein detecting similarity or difference between the one or more electrical parameters derived from the first and second resonant responses, wherein the electrical parameters are Q-factor measurements, comprises:
   computing difference quantity $\Delta Q$ as the difference between a second Q-factor derived from the second resonant response and a first Q-factor derived from the first resonant response; and
   indicating that, if the reference sample contains the molecular event and if the difference quantity $\Delta Q$ does not exceed a predefined value, the test sample includes the molecular event.

4. The method of claim 1, wherein providing a resonant test structure comprises providing a resonant coaxial probe.

5. The method of claim 1, wherein obtaining a first resonant response and deriving one or more electrical parameters are performed prior to the act of measuring a second resonant response, the method further comprising storing the one or more electrical parameters derived from the first resonant response in a database.

6. The method of claim 1, wherein obtaining first and second resonant responses comprises obtaining first and second input s-parameter responses at one or more frequencies in the range of 10 MHz and 1000 GHz.

7. The method of claim 1, wherein detecting similarity or difference between the one or more electrical parameters derived from the first and second resonant responses, wherein the electrical parameters are Q-factor measurements, comprises:
   computing difference quantity $\Delta Q$ as the difference between a second Q-factor derived from the second resonant response and a first Q-factor derived from the first resonant response; and
   indicating that, if the reference sample does not contain the molecular event and if the difference quantity $\Delta Q$ does not exceed a predefined value, the test sample excludes the molecular event.

8. The method of claim 5, further comprising retrieving the one or more electrical parameter derived from the first resonant response from the database.

9. The method of claim 1, wherein detecting similarity or difference between the one or more electrical parameters derived from the first and second resonant responses, wherein the electrical parameters are resonant frequency measurements, comprises:
   computing a difference quantity $\Delta f_{res}$ as the difference between a second resonant frequency derived from the second resonant response and a first resonant frequency derived from the first resonant response; and
   indicating that, if the reference sample contains the molecular event and if the difference quantity $\Delta f_{res}$ does not exceed a predefined value, the test sample includes the molecular event.

10. The method of claim 1, wherein detecting similarity or difference between the one or more electrical parameters derived from the first and second resonant responses, wherein the electrical parameters are resonant frequency measurements, comprises:
    computing a difference quantity $\Delta f_{res}$ as the difference between a second resonant frequency derived from the second resonant response and a first resonant frequency derived from the first resonant response; and
    indicating that, if the reference sample does not contain the molecular event and if the difference quantity $\Delta f_{res}$ does not exceed a predefined value, the test sample excludes the molecular event.

11. The method of claim 9, wherein obtaining a first resonant response and deriving a first resonant frequency are performed prior to obtaining a second resonant response, the method further comprising storing the first resonant frequency in a database.

12. The method of claim 11, further comprising retrieving the first resonant frequency from the database.

13. A system configured to detect a molecular event in a test sample, the system comprising:
    a test structure having a measureable signal response when a test signal is input and an output signal is recovered, wherein the measureable signal response is a resonant response;
    means for obtaining a first resonant response of the test structure when the test structure is electromagnetically coupled to a reference sample;
    means for obtaining a second resonant response of the test structure when the test structure is electromagnetically coupled to the test sample;
    means for deriving one or more electrical parameters from the first resonant response;
    means for deriving one or more electrical parameters from the second resonant response; and
    means for detecting similarity or difference between the one or more electrical parameters derived from the first and second resonant responses as an indication of the molecular event in the test sample.

14. The system of claim 13 wherein the resonant test structure comprises a resonant coaxial probe.

15. The system of claim 13, wherein the means for obtaining the first and second resonant responses each comprise a vector network analyzer.

16. The system of claim 13, wherein the means for obtaining the first and second resonant responses each comprise a scalar network analyzer.

17. The system of claim 13, wherein the means for deriving a first resonant frequency from the first resonant response and a second resonant frequency from the second resonant response comprises an automated network analyzer.

18. The system of claim 13, wherein the means for detecting a difference between the first and second electrical parameters comprises a computer.

19. The system of claim 13 wherein the one or more electrical parameters comprise s-parameter measurements, Q-factor measurements, or resonant frequency measurements.

20. A computer program product stored on a computer-readable medium and operable to control a test system to detect a molecular event in a test sample, the computer program product comprising:
   code that directs the test system to obtain a first resonant response of a test structure when the test structure is electromagnetically coupled to a reference sample;
   code that directs the test system to obtain a second resonant response of the test structure when the test structure is electromagnetically coupled to the test sample;
   code that directs the test system to derive one or more electrical parameters from the first resonant response;
   code that directs the test system to derive one or more electrical parameters from the second resonant response; and
   code that directs the test system to detect similarity or difference between the one or more electrical parameters derived from the first and second resonant responses as an indication of the molecular event in the test sample.

21. The computer program product of claim 20, wherein code that directs the test system to obtain first and second resonant responses comprises code that directs the test system to obtain first and second input s-parameters of the test structure when electromagnetically coupled to the reference and test samples, respectively.

22. The computer program product of claim 21, wherein code that directs the test system to derive one or more electrical parameters from the first and second resonant responses, respectively, comprises code that directs the test system to derive first and second resonant frequencies from the first and second resonant responses, respectively.

23. The computer program product of claim 21, wherein code that directs the test system to derive one or more electrical parameters from the first and second resonant responses, respectively, comprises code that directs the test system to derive first and second Q-factors from the first and second resonant responses, respectively.

24. The computer program product of claim 23, wherein code that directs the test system to detect similarity or difference between the first and second Q-factors comprises code that directs the test system to detect a difference between the first and second Q-factors.

25. The computer program product of claim 23, further comprising:
   code that directs the test system to derive a first resonant frequency from the first resonant response; and
   code that directs the test system to derive a second resonant frequency from the second resonant response.

26. The computer program product of claim 25, further comprising code that directs the test system to detect a difference between the first and second resonant frequencies.

27. A computer readable database stored in a computer readable medium for storing data indicating a molecular event within a reference sample, the computer readable database including one or more data structures operable to store data comprising first data representing the Q-factor of a test structure when the test structure is electromagnetically coupled to the reference sample.

28. The computer readable database of claim 27, further comprising second data representing the resonant frequency of the test structure when the test structure is electromagnetically coupled to the reference sample.

29. The computer readable database of claim 27, further comprising third data representing the temperature of the reference sample when the test structure is electromagnetically coupled to the reference sample.

30. The computer readable database of claim 27, further comprising fourth data representing the composition of the reference sample when the test structure is electromagnetically coupled to the reference sample.

31. The computer readable database of claim 27, further comprising fifth data representing the pH of the reference sample when the test structure is electromagnetically coupled to the reference sample.

* * * * *